(12) United States Patent
Fang

(10) Patent No.: US 9,243,303 B2
(45) Date of Patent: Jan. 26, 2016

(54) METHOD FOR THE DISSOLVING AND RAPID HYDROLYZING OF LIGNOCELLULOSE BIOMASS, DEVICE THEREOF AND USE OF THE SAME

(75) Inventor: Zhen Fang, Yunnan (CN)

(73) Assignee: XISHUANGBANNA TROPICAL BOTANICAL GARDEN, CHINESE ACADEMY OF SCIENCES, Yunnan (CN)

( * ) Notice: Subject to any disclaimer, the term of this patent is extended or adjusted under 35 U.S.C. 154(b) by 402 days.

(21) Appl. No.: 13/876,941

(22) PCT Filed: Jul. 4, 2011

(86) PCT No.: PCT/CN2011/001099
§ 371 (c)(1),
(2), (4) Date: Jul. 2, 2013

(87) PCT Pub. No.: WO2012/040995
PCT Pub. Date: Apr. 5, 2012

(65) Prior Publication Data
US 2013/0274527 A1    Oct. 17, 2013

(30) Foreign Application Priority Data
Sep. 30, 2010   (CN) .......................... 2010 1 0297515

(51) Int. Cl.
*C07C 29/00*   (2006.01)
*C09K 3/00*    (2006.01)
*C13K 1/02*    (2006.01)
*C08H 8/00*    (2010.01)
*C12P 7/10*    (2006.01)

(52) U.S. Cl.
CPC . *C13K 1/02* (2013.01); *C07C 29/00* (2013.01); *C08H 8/00* (2013.01); *C12P 7/10* (2013.01); *C09K 3/00* (2013.01); *C12P 2201/00* (2013.01); *C12P 2203/00* (2013.01); *Y02E 50/16* (2013.01); *Y02E 50/17* (2013.01)

(58) Field of Classification Search
CPC ....................................................... C09K 3/00
USPC ..................................... 252/183.11; 422/198
See application file for complete search history.

(56) References Cited

U.S. PATENT DOCUMENTS

2010/0270499 A1   10/2010 Fang et al.
2012/0067342 A1   3/2012  Fang

FOREIGN PATENT DOCUMENTS

| CN | 101235095 A | 8/2008 |
| CN | 101824156 A | 9/2010 |
| JP | 2001-095594 A | 4/2001 |
| KR | 100901296 B1 | 6/2009 |

OTHER PUBLICATIONS

English language abstract for CN 101235095 extracted from espacenet.com database on Jun. 17, 2013, 1 page.
English language abstract for CN 101824156 extracted from espacenet.com database on Jun. 17, 2013, 1 page.
English language abstract for KR 100901296 extracted from espacenet.com database on Jul. 8, 2013, 1 page.
English language abstract and translation for JP 2001-095594 extracted from PAJ database on Jul. 8, 2013, 23 pages.
International Search Report for Application No. PCT/CN2011/001099 dated Sep. 16, 2011, 9 pages.
Mitsuru Saski et al., "Kinetics of Cellulose Conversion at 25 MPa in Sub- and Supercritical Water", American Instiutue of Chemical Engineers, vol. 50 No. 5, Jan. 2004, pp. 192-194.
Liang, Jianghua, "Study on the Preparation of Fuel Ethanol from Lignocellulose under Bio-degradation with Ultasonic", Science-Engineering (I), China Master Theses Full-Text Database, No. 4, 2009, Apr. 15, 2009, p. 24, lines 1-3 and pp. 25-26.
R. Hashaikeh et al., "Hydrothermal Dissolution of Willow in Hot Compressed Water As a Model for Biomas Convesrsion", Fuel 86 (2007), Nov. 29, 2006, pp. 1621-1622.
Mitsuru Saski et al., "Dissolution and hydrolysis of Cellulose in Subcritical and Supercritical Water", Ind. Eng. Chem. Res. vol. 39, No. 8, Aug. 7, 2000.
Mitsuru Saski et al., "Fractionation of Sugarcane Bagasse by Hydrothermal Treatment", Bioresource Technology 86, 2003, pp. 301-304.
Katsunobu Ehara et al., "A Comparative Study on Chemical Conversion of Cellulose Between the Batch-Type and Flow-Type Systems in Supercritical Water", Cellulose 9, 2002, pp. 301-311.
William Shu-Lai Mok et al., "Uncatalyzed Solvolysis of Whole Biomass Hemicellulose by Hot Compressed Liquid Water", Ind. Eng. Chem. Res. vol. 31, No. 4, 1992, pp. 1157-1161.

*Primary Examiner* — Elvis O Price
(74) *Attorney, Agent, or Firm* — Howard & Howard Attorneys PLLC

(57) ABSTRACT

A method for the dissolving and rapid hydrolyzing of the lignocellulose biomass and the device thereof are disclosed. The lignocellulose biomass is put in the pure water and rapidly heated to 330~403° C., and then 89~99% of the lignocellulose biomass is dissolved and rapidly hydrolyzed to saccharide in 3.38~21.79 s. The following hydrolysis reaction can be carried out under the homogeneous phase condition for the dissolving of the lignocellulose biomass. At the same time, the solvated biomass could be easily used in the high pressure flow reactor to continuously pretreat the biomass and hydrolyze for producing saccharide, other biofuel and product. The present invention doesn't need any catalyst and doesn't pollute the environment, furthermore the process is simple and the cost is low, and it belongs to green, continuable industry encouraged by the state, and a good prospect of market application could be taken on.

9 Claims, 4 Drawing Sheets

METHOD FOR THE DISSOLVING AND RAPID HYDROLYZING OF LIGNOCELLULOSE BIOMASS, DEVICE THEREOF AND USE OF THE SAME

RELATED APPLICATIONS

This application is the National Stage of International Patent Application No. PCT/CN2011/001099, filed on Jul. 4, 2011, which claims priority to and all the advantages of Chinese Patent Application No. CN 201010297515.4, filed on Sep. 30, 2010, the content of which is incorporated herein by reference.

TECHNICAL FIELD

The present invention relates to the technical field of dissolving and hydrolyzing biomass, and particularly to a method for dissolving and rapidly hydrolyzing lignocellulose biomass. Meanwhile, the present invention also relates to a device used in the method for rapidly hydrolyzing and to the further application.

BACKGROUND ART

Lignocellulose biomass in the natural world, such as wood and grasses, is roughly composed of 50% cellulose, 25% hemicellulose and 20% lignin. Cellulose is mainly used for papermaking. Meanwhile, cellulose and hemicellulose can be degraded by hydrolysis to saccharides which are then used for producing ethanol. The existing methods for dissolving lignocellulose biomass mainly use a batch or semi-flow percolating reactor to carry out the dissolution reaction at a temperature of 200~300° C. for 15 minutes. Only approximately 40~60% of wood or grasses can be dissolved and hydrolyzed to hydrosoluble substances by using such methods. Thus, the methods are not only very low in production efficiency, but also too long in reaction time, which easily results in secondary decomposition of the saccharide products. The latest researches show that high-pressure hot water is a weakly polar solvent exhibiting both acidic and basic properties, and therefore can dissolve biomass and enables the hydrolysis reaction to occur in homogeneous phase. Sasaki et al. found that cellulose can be completely dissolved in water at 320° C. and at a water density of more than 1000 kg/m$^3$ (Sasaki, M.; Fang, Z.; Fukushima, Y.; Adschiri, T. & Arai, K. "Dissolution and hydrolysis of cellulose in subcritical and supercritical water", *Ind. Eng. Chem. Res.* 39, 2883-2890, 2000). Later, Ogihara et al. further found that, over a range of water densities of 550~1000 kg/m$^3$, for the temperatures at which cellulose is completely dissolved, there is a minimum of 320° C. at water density of 850 kg/m$^3$ (Ogihara Y.; Smith Jr., R. L.; Inomata H. & Kunio A., "Direct observation of cellulose dissolution in subcritical and supercritical water over a wide range of water densities (550~1000 kg/m$^3$), *Cellulose*, 12, 595-606, 2005). However, the above findings are all directed to pure cellulose, and thus are hard to be applied in industry because natural wood or grasses only contain about 50% cellulose and the process for separating cellulose is complicated and costly. Therefore, the technical problem that needs to be solved urgently in the art is how to realize the dissolution and rapid hydrolysis of natural lignocellulose biomass. On this basis, the present inventor found by study that the addition of an alkaline solution in pure water enables lignocellulose biomass such as wood flour to be completely dissolved and homogeneously hydrolyzed at 329° C.~367° C. A Chinese Patent Application was then filed accordingly (No. 200710141265.3). The addition of an acidic or an alkaline solution also enables cellulose to be completely dissolved and homogeneously hydrolyzed at a relatively low temperature (for example, 261~352° C.) (No. 201010104133.5). In the above methods, however, after adding an acidic or an alkaline catalyst solution, the production cost will be increased, the catalyst will not be recovered so easily and the environment will be polluted easily.

CONTENTS OF THE INVENTION

An object of the invention is to overcome the drawbacks of the prior art by providing a method for dissolving and rapidly hydrolyzing lignocellulose biomass. Said method is simple to implement, low-cost, and can be carried out in a manner of continuous industrial production.

Another object of the invention is to provide a device for the implementation of the aforesaid method for rapidly hydrolyzing.

Still another object of the invention is to provide the further application of the aforesaid method for rapidly hydrolyzing lignocellulose biomass, in industrial production.

The objects of the present invention are achieved through the following technical solution.

*Unless indicated elsewhere, the percentages used here are volume-based.

The technical solution of the invention is based on the inventor's following findings through his deep researches that lignocellulose can be dissolved and rapidly hydrolyzed by the following procedure: before lignocellulose biomass is hydrolyzed, it is firstly placed in pure water, and then the resultant mixture is mixed with high temperature hot water, and heated to a certain temperature at a certain heating rate. Therefore, the use of an acidic or basic catalyst solution is avoided, and the drawbacks of the prior art are overcome in a very simple manner.

A method for dissolving and rapidly hydrolyzing lignocellulose biomass comprises the following steps:

1. placing the lignocellulose biomass in pure water in a solid/liquid volume ratio of 0.003~1.05:1;
2. heating pure water to a temperature of 330~403° C.;
3. mixing the products obtained in steps 1 and 2 and putting the resultant mixture into a reactor, while keeping the biomass concentration in the mixture at 0.1~51.5%, setting the pressure at 19~416 MPa or water density at 523~905 kg/m$^3$, and heating the mixture to 330~403° C. at a heating rate of 7~10° C./s, whereby 89~99% of the lignocellulose biomass is hydrolyzed.

Said lignocellulose biomass includes: woody plants, such as willow wood flour and pine wood flour; or herbaceous plants, such as miscanthus.

The above method for rapidly hydrolyzing lignocellulose biomass can be used in the production of ethanol. Specifically, the lignocellulose biomass, after hydrolyzed, is further heated to 403° C. while keeping the heating rate, and then is freely cooled to room temperature. A majority of cellulose and hemicellulose in the biomass are hydrolyzed into saccharides including monosaccharides or oligosaccharides, which are used in the production of ethanol.

The invention also relates to a device for rapidly hydrolyzing lignocellulose biomass, characterized in that a pure water vessel is connected to a feed inlet of a reactor via a high pressure pump; a preheater is installed between the high pressure pump and the feed inlet of the reactor; a biomass material vessel is connected to a pure water pipe at the feed inlet of the reactor via a high pressure slurry pump; a heating unit is installed outside of the reactor; an ultrasonic generator is installed inside of the reactor; a resultant product vessel is connected to an outlet of the reactor via a pressure regulating valve, a solid/liquid separator and a cooler.

The reactor is a tubular continuous reactor.

As compared with the prior art, the invention has the advantages of excluding the use of any catalyst and therefore lowering the production cost, and effectively reducing the environmental pollution. As lignocellulose biomass is dissolved in water, the subsequent hydrolysis reaction can be carried out under the condition of a homogeneous phase, which greatly promotes the hydrolysis reaction and inhibits a thermal decomposition reaction. The total duration of the dissolution and hydrolysis reaction is less than 22 seconds. It will take only 3.38~21.79 s to dissolve and rapidly hydrolyze 89~99% of lignocellulose biomass. At the same time, the solvated lignocellulose biomass can be conveniently applied to a high pressure flow reactor, and can be hydrolyzed continuously to produce saccharides and other bio-fuels and products. The device for dissolving and hydrolyzing of the present invention permits rapidly mixing the lignocellulose biomass with the preheated high-temperature pure water stream and therefore the heating rate is very high (for example, possibly being heated to 400° C. in 0.4 s). Thus, the lignocellulose biomass can be heated rapidly to the dissolving and hydrolyzing temperature and thus a decomposition is avoided, and then a homogeneous reaction is further carried out.

MODE OF CARRYING OUT THE INVENTION

The invention is further illustrated in detail below by combining the figures and examples, which however are not to limit the technical solution of the invention. The lignocellulose material which can be used in the invention can be woody plants or herbaceous plants. Willow and pine are the representatives of the woody plants such as hardwood (18~25% lignin, 24~40% hemicellulose and 40~55% cellulose) and softwood (25~35% lignin, 25~35% hemicellulose and 45~50% cellulose). Miscanthus is the representative of herbaceous plants (containing 10~30% lignin, 35~50% hemicellulose and 25~40% cellulose). Willow wood flour is used as main test samples, which contains 22.7% lignin, 26.7% hemicellulose and 49.6% cellulose. In addition, pine wood flour (29% lignin, 26% hemicellulose and 44% cellulose) and miscanthus particles (20% lignin, 21% hemicellulose and 43% cellulose) are also used as test samples.

Willow wood flour, pine wood flour and miscanthus particles (particle size≤500 μm) are used in the following examples to illustrate the invention. However, as is known by a person skilled in the art, the lignocellulose biomass applicable to the invention are not limited to them, and various kinds of woody plants such as hardwood and softwood as well as various kinds of herbaceous plants can be used in the invention.

EXAMPLES

In order to better understand the essence of the invention, tests of the complete dissolution of willow wood flour are used to illustrate the technical effect of the invention and its application prospect in industrial production.

Figure 1:
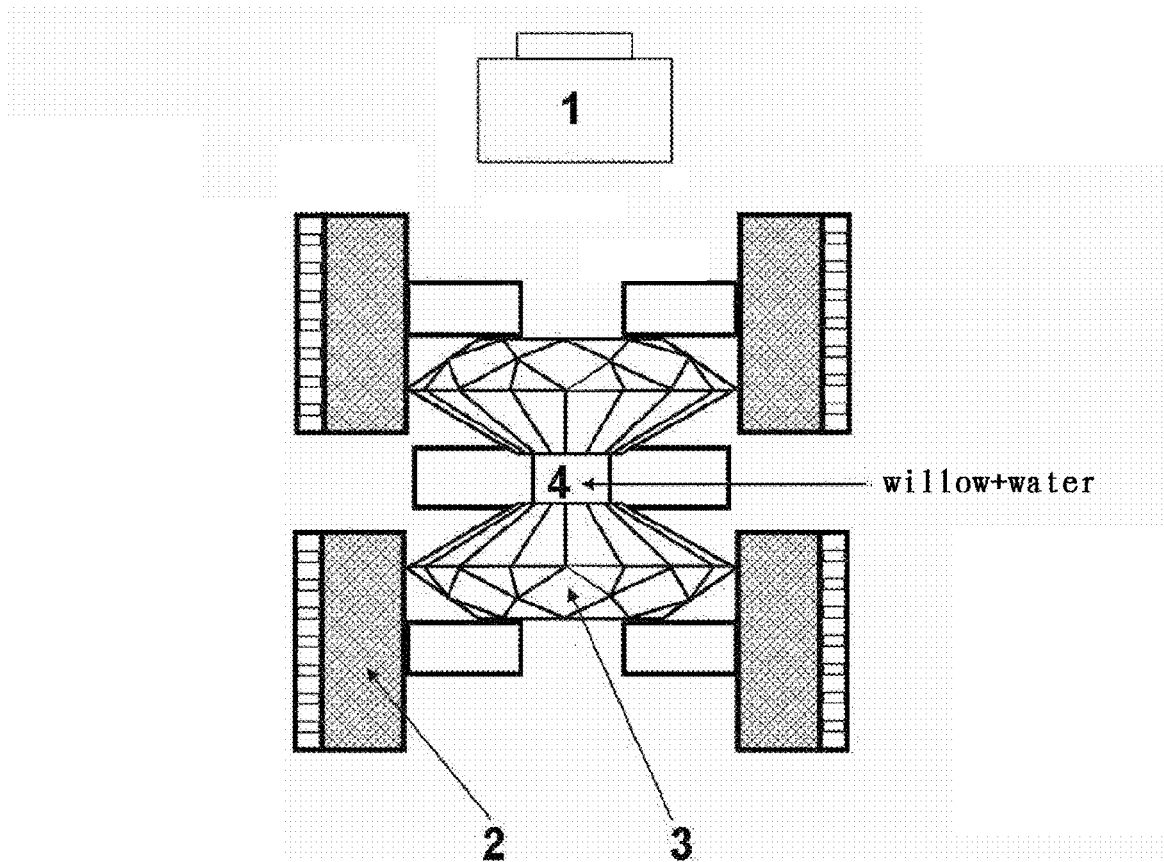
FIG. 1 is a schematic diagram of the structure of a visual micro-reactor Diamond Anvil Cell (DAC) used in the tests of the invention.

As shown in FIG. 1, the test device is a visual micro-reactor Diamond Anvil Cell (DAC), which can rapidly heat water in the reaction chamber to a high temperature, and the evolution of dissolution and hydrolysis of the wood flour can be observed. One small hole having a diameter of 500 μm is opened on an iron sheet of 250 μm in thickness, forming a reaction chamber 4 having a volume of 50 nL. After water and wood (or grasses) flour are filled in the reaction chamber 4, the small hole is compressed by two diamonds 3, the upper one and the lower one, and is sealed to produce pressure. By loosening these two diamonds, nitrogen gas is allowed to enter into the small hole and generate gas bubbles. Different water densities (water density=water mass/reactor volume, kg/m$^3$) can be obtained by adjusting the size of the gas bubbles. Water in the reaction chamber is heated rapidly by an electrical heater 2 and meanwhile is observed and video-recorded under a common optical microscope 1 with 110× magnification. After the reaction, the resultant products remaining on the surface of the diamonds are analyzed by an infrared microscope for their chemical structure. Since the volume of the reaction chamber is constant, pressure can be calculated according to the equation of state using the known water density and the temperature of the reactor (measured by thermocouples). 4 mL of willow wood flour (particle size≤500 μm) and 4 mL of pure water are weighed.

Test 1

The heating rate is set to 10° C./s and the water density is 523 kg/m$^3$. Willow wood flour (length=500 μm) and pure water are added so that the concentration of the wood flour is 51.5%.

a: Before heated, willow wood flour is suspended in water and gas bubbles.

b: When heated to 294° C. at 21.92 s, the wood flour begins to dissolve, as indicated by yellowing of the water.

c: When heated to 326° C. at 25.48 s, main dissolution begins until 343° C. after further 2.67 s.

d. At 30.55 s, gas bubbles disappear and the water density is calculated as 523 kg/m$^3$. At this time, 84% of wood flour is dissolved in pure water, but an insoluble solid residue is remained.

e: At 38.5 s, as the temperature is further increased to the maximum of 403° C. (or the pressure of 42 MPa), 89% of wood flour is dissolved in pure water. The residue becomes black due to carbonization. The wood flour dissolved in water undergoes a hydrolysis reaction accompanied by color change of the solution from yellow to red.

Figure 6:
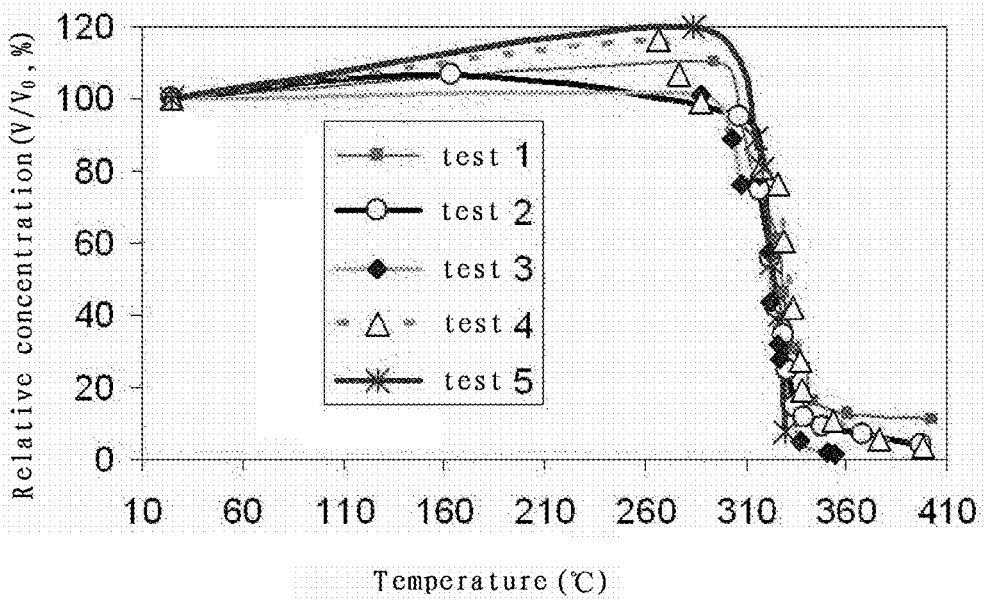
FIG. 6 shows the change in relative concentration of willow wood flour as a function of the heating temperature (Tests 1-5) ($V_0$—initial volume concentration, V—immediate volume concentration).

The variation in relative concentration of the willow wood flour as a function of the heating temperature (Test 1) ($V_0$—initial volume concentration, V—immediate volume concentration) is shown in FIG. 6.

Figure 7:
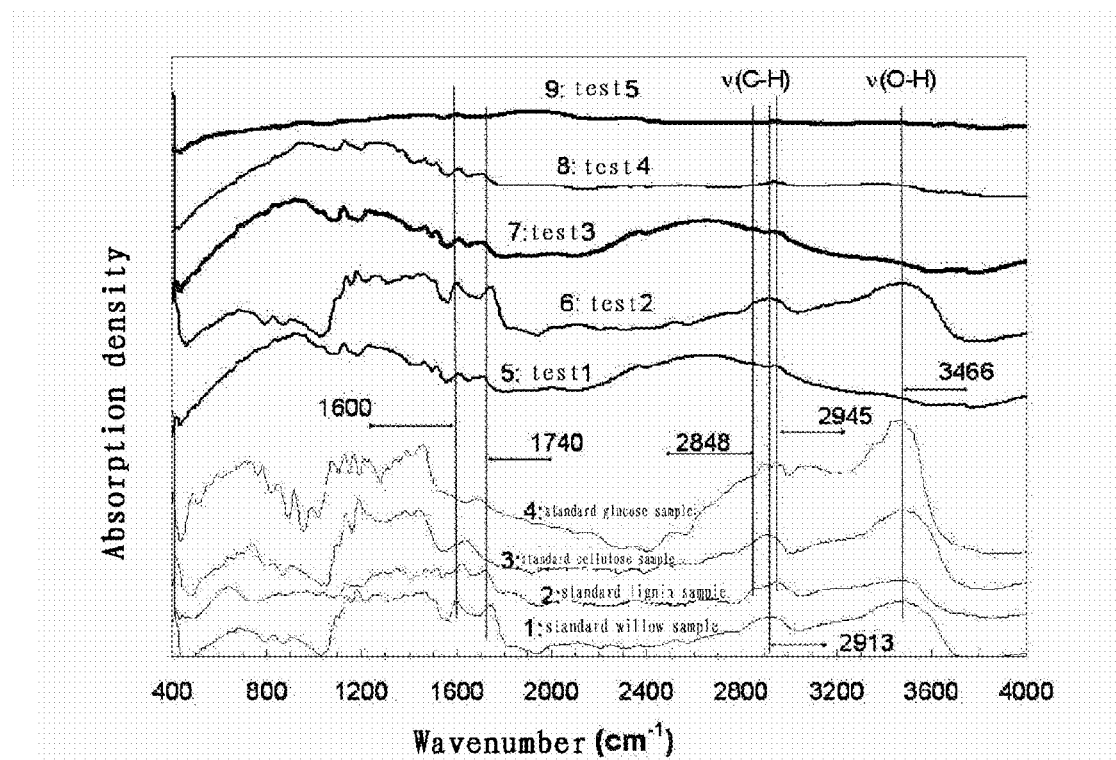
FIG. 7 shows the absorption curves of Infrared spectra of the test products (Tests 1-5).

After reaction, the reactor is opened and saccharide-like products are remained on surface of the diamonds. IR analysis shows that the products have been hydrolyzed and have the characteristics of glucose (FIG. 7; curve 5 vs. curves 1-4).

Conclusion: Rapid heating of low density water (523 kg/m$^3$) enables most of wood flour (89%) to be dissolved and hydrolyzed into saccharides, but there are still some solids remained.

Test 2

The heating rate is set to 9° C./s and the water density is 905 kg/m$^3$. Willow wood flour (length<500 µm) and pure water are added so that the concentration of the wood flour is 34.3%.

Figure 2:
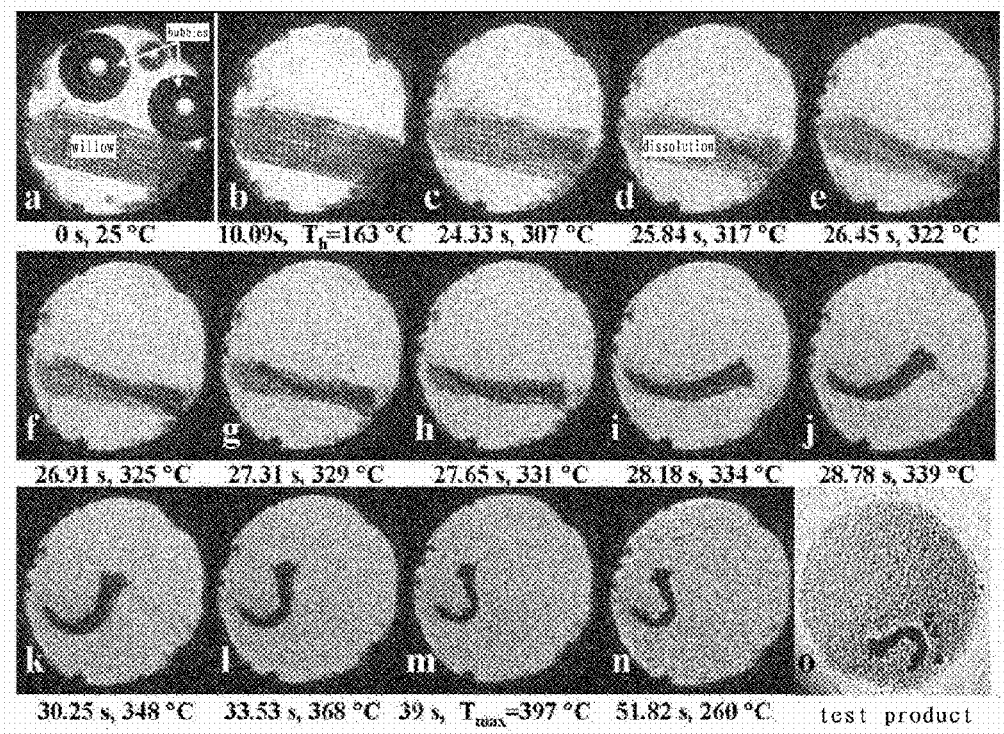
FIG. 2 (Test 2) gives common optical microphotographs showing the evolution of dissolution and hydrolysis of willow wood flour (length≤500 μm; concentration=34.3%) in pure water during the heating of willow wood flour and pure water to 397° C. and 416 MPa (heating rate=9° C./s, water density=905 kg/m$^3$).

As shown in FIG. 2:

a: Before heated, willow wood flour is suspended in water and gas bubbles.

b: When heated to 163° C. at 10.09 s, gas bubbles disappear and the water density is calculated as 905 kg/m$^3$.

c: When heated to 307° C. at 24.33 s, the wood flour begins to dissolve, as indicated by yellowing of the water.

d-i: When heated to 317° C. at 25.84 s, main dissolution begins until 334° C. after further 2.34 s. 85% of wood flour is dissolved in pure water, but an insoluble solid residue is remained, which gradually becomes black since 317° C.

j-m: At 28.78 s, numerous black fine particles precipitate. As the temperature is further increased to the maximum of 397° C. (or the pressure of 416 MPa), 96% of wood flour is dissolved in pure water. The residue becomes black due to carbonization. The wood flour dissolved in water undergoes a hydrolysis reaction and a thermal decomposition reaction.

The variation in relative concentration of the willow wood flour as a function of the heating temperature (Test 2) ($V_0$—initial volume concentration, V—immediate volume concentration) is shown in FIG. 6.

After reaction, the reactor is opened and saccharide-like products, numerous black fine particles and a black solid residue are remained on surface of the diamonds (FIG. 2-o). IR analysis shows that the saccharide-like products have been hydrolyzed and have the characteristics of glucose (FIG. 7; curve 6 vs. curves 1-4).

Conclusion: Rapid heating of high density water (905 kg/m$^3$) enables most of wood flour (96%) to be dissolved and hydrolyzed into saccharides, but the secondary thermal decomposition occurs more easily.

Test 3

The heating rate is set to 8° C./s and the water density is 571 kg/m$^3$. Smaller willow wood flour (length≤200 µm) and pure water are added so that the concentration of the wood flour is 47.5%.

Figure 3:
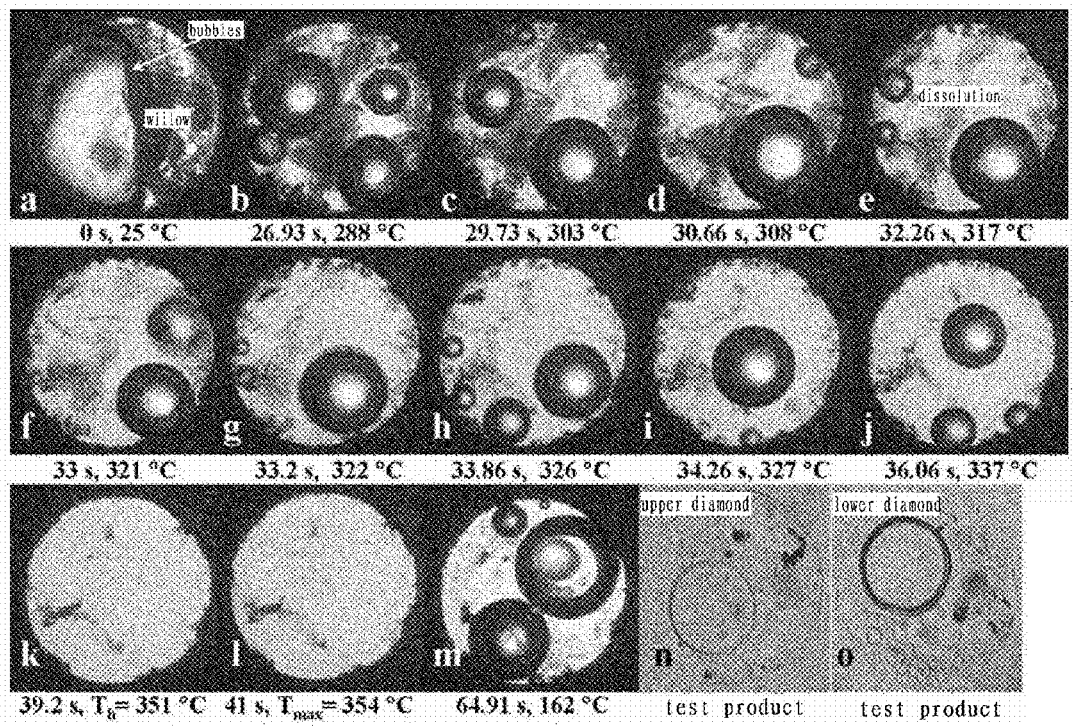
FIG. 3 (Test 3) gives common optical microphotographs showing the evolution of dissolution and hydrolysis of willow wood flour (length≤200 μm; concentration=47.5%) in pure water during the heating of willow wood flour and pure water to 354° C. and 19 MPa (heating rate=8° C./s, water density=571 kg/m$^3$).

As shown in FIG. 3:

a: Before heated, willow wood flour is suspended in water and gas bubbles.

b-c: When heated to 303° C. at 29.73 s, the wood flour begins to dissolve, as indicated by yellowing of the water.

d-j: When heated to 317° C. at 32.26 s, main dissolution begins until 337° C. after further 3.8 s. 95% of wood flour is dissolved in pure water, but a tiny insoluble solid residue is remained.

k: When heated to 351° C. at 39.2 s, gas bubbles disappear and the water density is calculated as 571 kg/m$^3$.

l: at 41 s, the temperature is further increased to the maximum of 354° C. (or the pressure of 19 MPa). 99% of wood flour is dissolved in pure water. The wood flour dissolved in water undergoes a hydrolysis reaction.

The variation in relative concentration of the willow wood flour as a function of the heating temperature (Test 3) ($V_0$—initial volume concentration, V—immediate volume concentration) is shown in FIG. 6.

After reaction, the reactor is opened and saccharide-like products are remained on surface of the diamonds (FIG. 3-n, o). IR analysis shows that the saccharide-like products have been hydrolyzed and have the characteristics of glucose (FIG. 7; curve 7 vs. curves 1-4).

Conclusion: Rapid heating of low density water (571 kg/m$^3$) enables most of wood flour (99%) to be dissolved and rapidly hydrolyzed into saccharides.

Test 4

The heating rate is set to 7° C./s and the water density is 736 kg/m$^3$. Willow wood flour (≤500 µm) and pure water are added so that the concentration of the wood flour is 35%.

Figure 4:
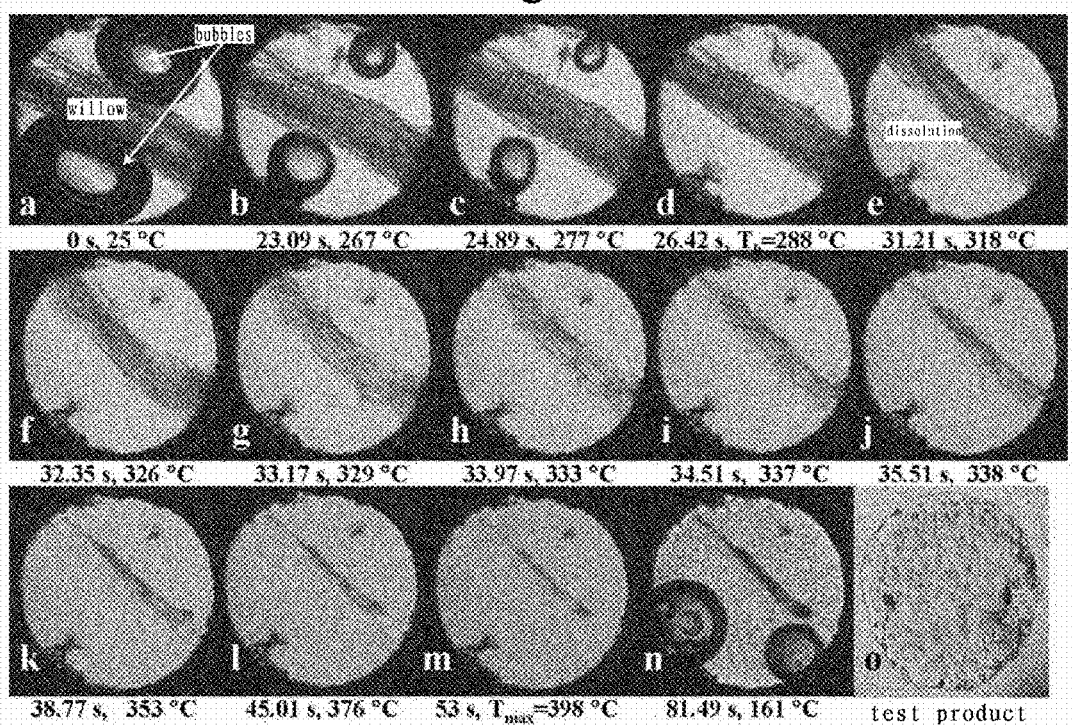
FIG. 4 (Test 4) gives common optical microphotographs showing the evolution of dissolution and hydrolysis of willow wood flour (length≤500 μm; concentration=35%) in pure water during the heating of willow wood flour and pure water to 398° C. and 132 MPa (heating rate=7° C./s, water density=736 kg/m$^3$).

As shown in FIG. 4:

a: Before heated, willow wood flour is suspended in water and gas bubbles.

d: When heated to 288° C. at 26.42 s, gas bubbles disappear and the water density is calculated as 763 kg/m$^3$.

e: When heated to 318° C. at 31.21 s, the wood flour begins to dissolve, as indicated by yellowing of the water.

e-k: When heated to 318° C., main dissolution begins until 353° C. after further 7.56 s. 89% of wood flour is dissolved in pure water, but an insoluble solid residue is remained.

m: At 53 s, the temperature is further increased to the maximum of 398° C. (or the pressure of 132 MPa). 96% of wood flour is dissolved in pure water. The wood flour dissolved in water undergoes a hydrolysis reaction.

The variation in relative concentration of the willow wood flour as a function of the heating temperature (Test 4) ($V_0$—initial volume concentration, V—immediate volume concentration) is shown in FIG. 6.

After reaction, the reactor is opened and saccharide-like products are remained on surface of the diamonds (FIG. 4-o). IR analysis shows that the saccharide-like products have been hydrolyzed and have the characteristics of glucose (FIG. 7; curve 8 vs. curves 1-4).

Conclusion: Rapid heating of medium density water (736 kg/m$^3$) enables most of wood flour (96%) to be dissolved and rapidly hydrolyzed into saccharides.

Test 5

The heating rate is set to 8° C./s and the water density is 743 kg/m$^3$. Smaller willow wood flour (length≤250 µm) and pure water are added so that the concentration of the wood flour is 27%.

Figure 5:
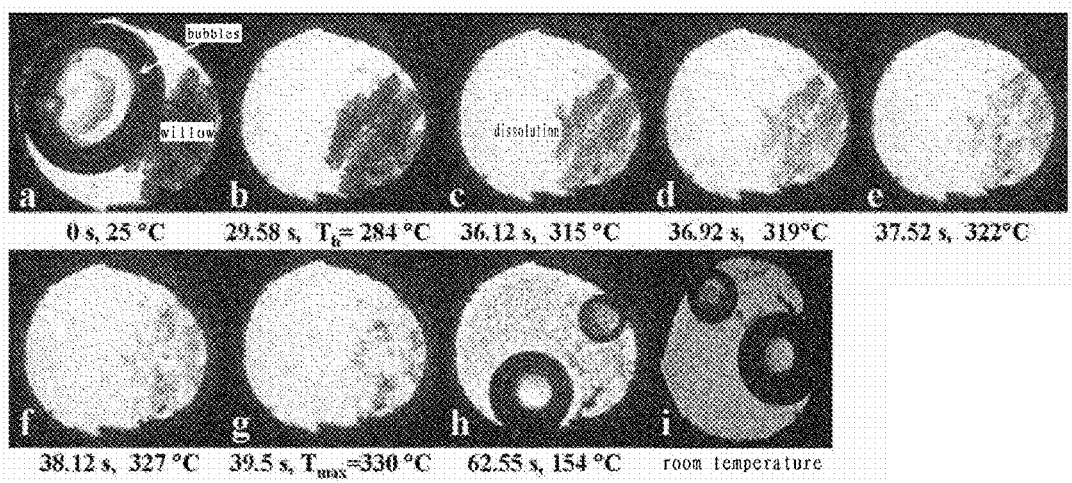
FIG. 5 (Test 5) gives common optical microphotographs showing the evolution of dissolution and hydrolysis of willow wood flour (length≤300 μm; concentration=27%) in pure water during the heating of willow wood flour and pure water to 330° C. and 59 MPa (heating rate=8° C./s, water density=743 kg/m$^3$).

As shown in FIG. 5:

a: Before heated, willow wood flour is suspended in water and gas bubbles.

b: When heated to 284° C. at 29.58 s, gas bubbles disappear and the water density is calculated as 743 kg/m$^3$.

c: When heated to 315° C. at 36.12 s, the wood flour begins to dissolve, as indicated by yellowing of the water.

c-g: When heated to 315° C., main dissolution begins until the maximum of 330° C. (or the pressure of 59 MPa) after further 3.38 s. 92% of wood flour is dissolved in pure water. The wood flour dissolved in water undergoes a hydrolysis reaction, but an insoluble solid residue is remained.

The variation in relative concentration of the willow wood flour as a function of the heating temperature (Test 5) ($V_0$—initial volume concentration, V—immediate volume concentration) is shown in FIG. 6.

After reaction, IR analysis shows that the saccharide-like products have been hydrolyzed and have the characteristics of glucose (FIG. 7; curve 9 vs. curves 1-4).

Conclusion: Rapid heating of medium density water (743 kg/m$^3$) enables most of wood flour (92%) to be dissolved and rapidly hydrolyzed into saccharides. However, as compared with low density water, medium density water has a poorer capacity of dissolving and hydrolyzing.

Example 1

Willow wood flour (length≤250 μm) is placed in pure water, so as to form a biomass material in which the solid/liquid volume ratio between the willow wood flour and the pure water is 0.6:1. Pure water is heated to 370° C., and then the pure water and the biomass material are mixed and put in a reactor. The concentration of the willow wood flour is 20% and the water density is set to 600 kg/m$^3$. The mixture is rapidly heated to 370° C. (the pressure of 34 MPa) at a heating rate of 8° C./s. At 315° C., main dissolution begins, and continues only for 6.88 s to dissolve and hydrolyze 90% of the willow wood flour.

Example 2

The Example 1 is repeated except that the solid/liquid volume ratio between the willow wood flour (particle size≤1 μm) and the pure water is 0.003:1; pure water is heated to 356° C.; after mixing, the concentration of the willow wood flour is 0.1% and the water density is set to 550 kg/m$^3$; the mixture is rapidly heated to 356° C. (the pressure of 18 MPa) at a heating rate of 10° C./s; at 320° C., main dissolution begins, and continues only for 3.6 s to dissolve and rapidly hydrolyze 95% of the willow wood flour.

Example 3

The Example 1 is repeated except that the biomass is pine wood flour (particle sizeparticle size≤200 μm) in which the solid/liquid volume ratio between the pine wood flour and the pure water is 1.05:1; pure water is heated to 380° C.; after mixing, the concentration of the pine wood flour is 35% and the water density is set to 700 kg/m$^3$; the mixture is rapidly heated to 380° C. (the pressure of 84 MPa) at a heating rate of 9° C./s; at 318° C., main dissolution begins, and continues only for 6.89 s to dissolve and rapidly hydrolyze 91% of the pine wood flour.

Example 4

The Example 1 is repeated except that the biomass is miscanthus flour (particle size≤300 μm) in which the solid/liquid volume ratio between the miscanthus flour and the pure water is 0.8:1; pure water is heated to 360° C.; after mixing, the concentration of the miscanthus flour is 26.7% and the water density is set to 723 kg/m$^3$; the mixture is rapidly heated to 360° C. (the pressure of 79 MPa) at a heating rate of 7° C./s; at 322° C., main dissolution begins, and continues only for 5.43 s to dissolve and rapidly hydrolyze 92% of the miscanthus flour.

Example 5

Figure 8:
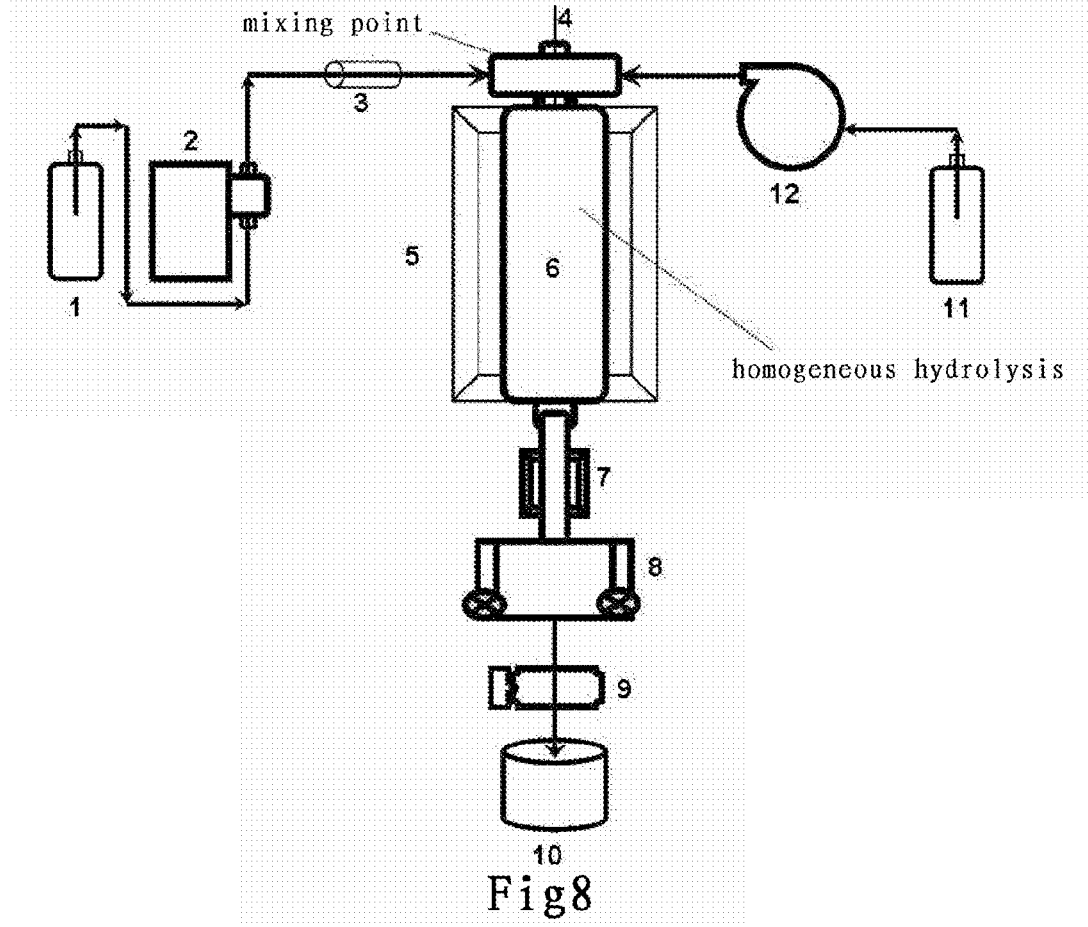
FIG. 8 is a schematic diagram of connection of the device of the invention, in which 1—pure water vessel; 2—high pressure pump; 3—preheater; 4—ultrasonic generator; 5—electrical heating furnace; 6—reactor; 7—cooler; 8—solid/liquid separator; 9—pressure regulating valve; 10—resultant product vessel; 11—biomass material vessel; 12—high pressure slurry pump.

A device for dissolving and rapidly hydrolyzing lignocellulose biomass is shown in FIG. 8. A pure water vessel 1 is connected to a feed inlet of a tubular reactor 6 via a high pressure pump 2. A preheater 3 is installed between the high pressure pump and the feed inlet of the tubular reactor. A biomass material vessel 11 is connected to a pure water pipe at the feed inlet of the tubular reactor 6 via a high pressure slurry pump 12. An electrical heating furnace 5 is installed outside of the tubular reactor 6 and an ultrasonic generator 4 is installed inside of the tubular reactor 6. A resultant product vessel 10 is connected to an outlet of the tubular reactor 6 via a pressure regulating valve 9, a solid/liquid separator 8 and a cooler 7.

The operating principle of the continuous process device is as follows. Pure water from the pure water vessel 1 is preheated to 330° C.~403° C. by the preheater 3 and is then pumped by the high pressure pump 2 into the tubular reactor 6. Lignocellulose biomass and pure water are mixed in the biomass material vessel 11, and then pumped by the high pressure slurry pump 12 to the location before the feed inlet of the tubular reactor 6 where the mixture is mixed with the preheated pure water, and then immediately enter into the tubular reactor 6 for rapidly heating. The lignocellulose biomass is dissolved and undergoes a rapid homogenous hydrolysis in the reactor. The ultrasonic generator 4 is used to promote the dissolution and hydrolysis. After solids are separated by the solid/liquid separator 8, the hydrosoluble hydrolysates are discharged from the outlet of the reactor and sent to the resultant product vessel 10. The cooling rate is controlled by the cooler 7 and the reaction pressure is controlled by the pressure regulating valve 9.

With the continuous process device, it is easy to control the reaction of the solvated biomass, such as reaction time, pressure and temperature and so on. The main applications are:

(1) Biomass Pretreatment

The structure of the biomass in a homogeneous phase is broken-down when the solvated biomass is further heated or is maintained for a longer time. After such pretreatment, the resultant polysaccharides can be used to produce ethanol or other bio-products by using a bioconversion method(for example, to produce by fermentation antibiotics, lysine, lactic acid and sodium glutamate, etc.).

(2) Complete Hydrolysis of Biomass to Saccharides and Phenols

Biomass will be homogeneously hydrolyzed to saccharides and phenols when the solvated biomass is heated to a higher temperature or is maintained for a longer time. The saccharides can be used to produce ethanol and the phenols can be used to produce biological plastics. The saccharides and the phenols can also be used to produce bio-products by bioconversion.

(3) Continuous Production of Gas, Liquid Fuels or Chemicals

By filling a catalyst in the rear part of the tubular reactor, the biomass, after dissolved, enters into the rear part to undergo a homogeneous catalytic reaction. As the solvated biomass is easily accessible to the active sites of the catalyst, the reaction occurs easily. The solvated biomass is catalyzed or non-catalyzed in liquid hot water to homogeneously produce gas (for example, to produce $H_2$ with Ni catalyst) and liquid (for example, to produce hydrocarbons with Pt catalyst) fuels and to synthesize chemicals (for example, to produce 5-hydroxymethylfurfural and furfural, to produce alcohols with Pt/—$Al_2O_3$ catalyst) and foodstuffs (for example, erythrose and pentose, etc.).

The invention claimed is:

1. A method for dissolving and rapidly hydrolyzing lignocellulose biomass, comprising the following steps:
    (1) placing the lignocellulose biomass in pure water in a solid/liquid volume ratio of 0.003 to 1.05:1;
    (2) heating pure water to a temperature of 330 to 403 C;
    (3) mixing the products obtained in steps (1) and (2) and putting the resultant mixture into a reactor, while keeping the biomass concentration in the mixture at 0.1 to 51.5%, setting the pressure at 19 to 416 MPa or water density at 523 to 905 kg/m$^3$, and heating the mixture to 330 to 403 C at a heating rate of 7 to 10 C/s, whereby 89 to 99% of the lignocellulose biomass is hydrolyzed.

2. A method of producing ethanol using lignocellulose biomass, said method comprising the following steps:
    hydrolyzing the lignocellulose biomass;
    heating the lignocellulose biomass, after hydrolyzing, to 403 C while keeping the heating rate; and then
    cooling to room temperature, wherein a majority of cellulose and hemicellulose in the lignocellulose biomass are hydrolyzed into saccharides, including monosaccharides or oligosaccharides, for the production of ethanol.

3. The method of producing ethanol using lignocelluloses biomass as claimed in claim 2, wherein the step of hydrolyzing comprises;
    (1) placing the lignocellulose biomass in pure water in a solid/liquid volume ratio of 0.003 to 1.05:1,
    (2) heating pure water to a temperature of 330 to 403° C.,
    (3) mixing the products obtained in steps (1) and (2) and putting the resultant mixture into a reactor, while keeping the biomass concentration in the mixture at 0.1 to 51.5%, setting the pressure at 19 to 416 MPa or water density at 523 to 905 kg/m$^3$, and heating the mixture to 330 to 403 C at a heating rate of 7 to 10 C/s, whereby 89 to 99% of the lignocellulose biomass is hydrolyzed.

4. The method for dissolving and rapidly hydrolyzing lignocellulose biomass as claimed in claim 1, wherein the reactor is further defined as a tubular reactor.

5. The method for dissolving and rapidly hydrolyzing lignocellulose biomass as claimed in claim 4, further comprising the steps of installing an ultrasonic generator in the tubular reactor and sonicating the mixture.

6. The method for dissolving and rapidly hydrolyzing lignocellulose biomass as claimed in claim 5, further comprising the step of adding a catalyst to a rear portion of the reactor.

7. The method for dissolving and rapidly hydrolyzing lignocellulose biomass as claimed in claim 4, further comprising the step of adding a catalyst to a rear portion of the reactor.

8. The method for dissolving and rapidly hydrolyzing lignocellulose biomass as claimed in claim 1, further comprising the steps of installing an ultrasonic generator in the reactor and sonicating the mixture.

9. The method for dissolving and rapidly hydrolyzing lignocellulose biomass as claimed in claim 8, further comprising the step of adding a catalyst to a rear portion of the reactor.

* * * * *